(12) United States Patent
Calisti et al.

(10) Patent No.: US 7,905,007 B2
(45) Date of Patent: Mar. 15, 2011

(54) METHOD FOR FORMING A MATCHING LAYER STRUCTURE OF AN ACOUSTIC STACK

(75) Inventors: Serge Gerard Calisti, Bouches du Rhone (FR); Frederic Lanteri, Le Cannet (FR); Lowell Smith, Niskayuna, NY (US); Charles Baumgartner, Niskayuna, NY (US); Jean-Francois Gelly, Mougins (FR)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 12/406,731

(22) Filed: Mar. 18, 2009

(65) Prior Publication Data

US 2010/0237746 A1 Sep. 23, 2010

(51) Int. Cl.
*H04R 31/00* (2006.01)
(52) U.S. Cl. ....... 29/594; 29/25.35; 29/592.1; 29/609.1; 310/311; 310/313 R; 310/334

(58) Field of Classification Search .................. 29/25.35, 29/592.1, 594, 609.1; 310/310, 313 R, 334
See application file for complete search history.

(56) References Cited

U.S. PATENT DOCUMENTS

| 4,153,135 A | 5/1979 | Bouyoucos |
| 4,779,020 A | 10/1988 | Konno et al. |
| 6,822,373 B1 | 11/2004 | Butler |
| 7,573,177 B2 * | 8/2009 | Fuller et al. .................. 310/311 |
| 2008/0196971 A1 * | 8/2008 | Charbonnier et al. ........ 181/290 |
| 2009/0219108 A1 * | 9/2009 | Zhao et al. ...................... 333/32 |

* cited by examiner

*Primary Examiner* — Paul D Kim
(74) *Attorney, Agent, or Firm* — Dean Small; The Small Patent Law Group

(57) ABSTRACT

An acoustical stack for an ultrasound probe comprises a piezoelectric layer having top and bottom sides and a plurality of matching layer sections forming a matching layer structure. Each of the matching layer sections comprises a spring layer comprising a first material and a mass layer comprising a second material that is different than the first material. The spring layer within the matching layer section that is positioned closest to the piezoelectric layer is thinner than the spring layer within the other matching layer sections.

11 Claims, 9 Drawing Sheets

US 7,905,007 B2

METHOD FOR FORMING A MATCHING LAYER STRUCTURE OF AN ACOUSTIC STACK

BACKGROUND OF THE INVENTION

The subject matter disclosed herein relates generally to ultrasound probes, and more particularly, to acoustical stacks within the ultrasound probes.

An ultrasound probe typically has many acoustical stacks that each correspond to an imaging element of the probe. Each acoustical stack has several layers that are attached together in a stacked configuration. A piezoelectric layer within the stack is formed of a piezoelectric material, such as piezoelectric ceramic, that has high impedance.

Matching layers are provided on the top side of the piezoelectric layer to transform the acoustic impedances between the piezoelectric layer that has high impedance and an exterior or lens of the probe that has low impedance. The low impedance may be based on the acoustic impedance of water, a human, or other subject to be scanned. Many probes include two matching layers based on quarter-wavelength matching wherein each of the matching layers is approximately one-quarter wavelength thick. Each quarter-wavelength matching layer acts to transform the impedance within a limited bandwidth. Using two quarter-wavelength matching layers limits the bandwidth range to between eighty and ninety percent. To achieve impedance matching in a larger bandwidth, a larger number of quarter-wavelength matching layers is needed. However, increasing the number of quarter-wavelength matching layers greatly increases the thickness of the stack and increases the signal attenuation. In addition, the stacked materials become increasingly difficult to dice, and it may be difficult to find appropriate materials for each of the quarter-wavelength matching layers while still controlling the desired geometry and impedances.

Additionally, a gradient or graded matching layer that uses a material with continuously changing impedance, or many layers of many different materials that have different acoustic impedances, has been proposed for use instead of the discrete quarter-wavelength matching layers. However, these graded matching layer configurations require that the overall thickness of the matching layer(s) be too thick. Good matching characteristics are only achieved if the thickness of the graded matching layer is in the range of at least one or two wavelengths. At this thickness, strong attenuation of the ultrasound signal occurs. The dicing operation is very difficult due to the thickness of the layer, as dicing is difficult for thicker layers but not for thin layers, and requires a high amount of blade exposure. If the graded matching layer has a thickness that is less than one wavelength, however, bad matching or ringing in the bandwidth will result.

BRIEF DESCRIPTION OF THE INVENTION

In one embodiment, an acoustical stack for an ultrasound probe comprises a piezoelectric layer having top and bottom sides and a plurality of matching layer sections forming a matching layer structure. Each of the matching layer sections comprises a spring layer comprising a first material and a mass layer comprising a second material that is different than the first material. The spring layer within the matching layer section that is positioned closest to the piezoelectric layer is thinner than the spring layer within the other matching layer sections.

In another embodiment, a method for forming a matching layer structure of an acoustical stack for an ultrasound probe comprises forming a first matching layer section comprising a spring layer at a bottom side of the first matching layer section and a mass layer at a top side of the first matching layer section. The bottom side of the first matching layer section is configured to be attached to one of a piezoelectric layer and a quarter-wavelength matching layer. The spring layer comprises a spring material and the mass layer comprising a mass material that has higher impedance than the spring material. At least one additional matching layer section is formed comprising a spring layer at a bottom side of the additional matching layer section and a mass layer at a top side of the additional matching layer section. The bottom side of the additional matching layer section is configured to be attached to the top side of the first matching layer section. The spring layer comprises the spring material and the mass layer comprises the mass material.

In yet another embodiment, a method for forming a matching layer structure of an acoustical stack for an ultrasound probe comprises forming a first matching layer section by forming a spring layer comprising a spring material and forming a mass layer comprising a mass material over the spring layer. The mass material has a higher density than the spring material. N matching layer sections are formed over the first matching layer section by forming spring layers comprising the spring material alternating with mass layers comprising the mass material.

DETAILED DESCRIPTION OF THE INVENTION

Figure 1:
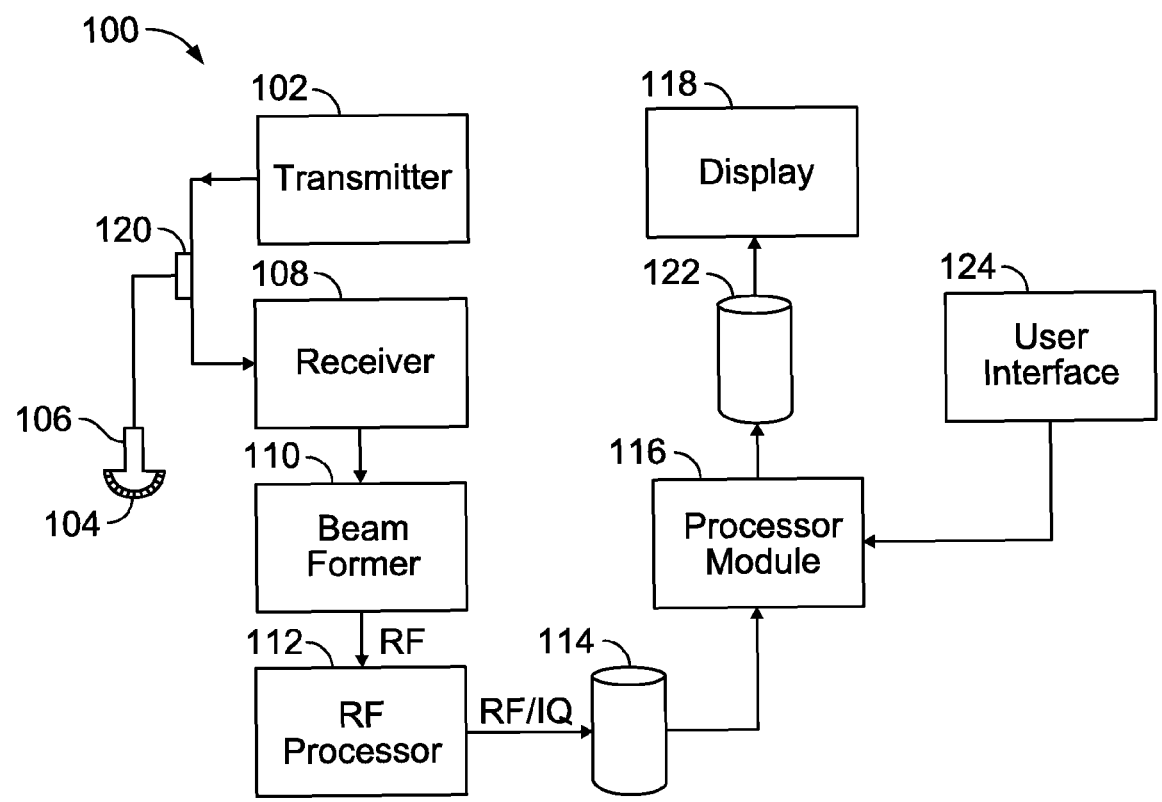
FIG. 1 illustrates an ultrasound system formed in accordance with an embodiment of the present invention.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Figure 5:
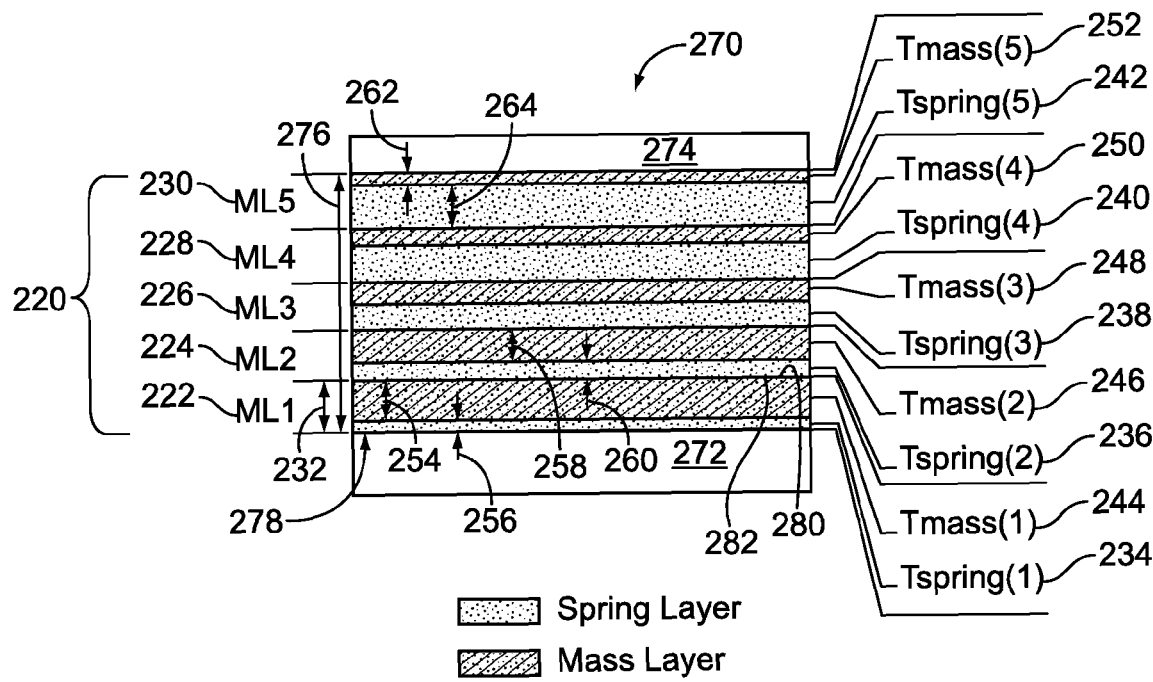
FIG. 5 illustrates a matching layer structure formed in accordance with an embodiment of the present invention for use within an ultrasound probe.
Figure 12:
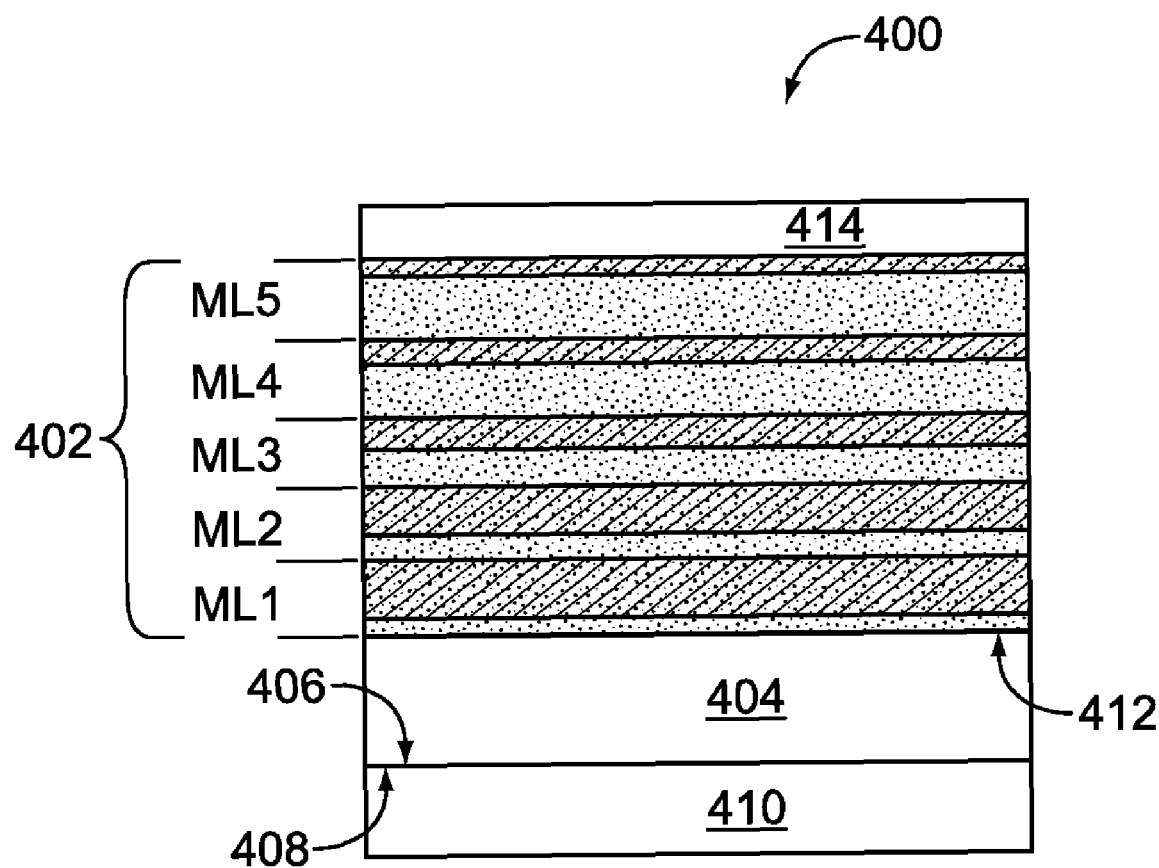
FIG. 12 illustrates an acoustical stack including both a matching layer structure and a quarter-wavelength matching layer formed in accordance with an embodiment of the present invention.

FIG. 1 illustrates an ultrasound system 100 including a transmitter 102 that drives an array of elements 104 (e.g., piezoelectric elements) within a probe 106 to emit pulsed ultrasonic signals into a body. The probe 106 may include a matching layer structure (as shown in FIGS. 5 and 12). The elements 104 may be arranged, for example, in one or two dimensions. A variety of geometries may be used. The system 100 may have a probe port 120 for receiving the probe 106 or the probe 106 may be hardwired to the system 100.

The ultrasonic signals are back-scattered from structures in the body, like fatty tissue or muscular tissue, to produce echoes that return to the elements 104. The echoes are received by a receiver 108. The received echoes are passed through a beamformer 110 that performs beamforming and outputs a radiofrequency (RF) signal. The RF signal then passes through an RF processor 112. Alternatively, the RF processor 112 may include a complex demodulator (not shown) that demodulates the RF signal to form in-phase and quadrature (IQ) data pairs representative of the echo signals. The RF or IQ signal data may then be routed directly to a memory 114 for storage.

The ultrasound system 100 also includes a processor module 116 to process the acquired ultrasound information (e.g., RF signal data or IQ data pairs) and prepare frames of ultrasound information for display on display 118. The processor module 116 is adapted to perform one or more processing operations according to a plurality of selectable ultrasound modalities on the acquired ultrasound information. Acquired ultrasound information may be processed and displayed in real-time during a scanning session as the echo signals are received. Additionally or alternatively, the ultrasound information may be stored temporarily in memory 114 or memory 122 during a scanning session and then processed and displayed in an off-line operation.

A user interface 124 may be used to input data to the system 100, adjust settings, and control the operation of the processor module 116. The user interface 124 may have a keyboard, trackball and/or mouse, and a number of knobs, switches or other input devices such as a touchscreen. The display 118 includes one or more monitors that present patient information, including diagnostic ultrasound images to the user for diagnosis and analysis. One or both of memory 114 and memory 122 may store two-dimensional (2D) and/or three-dimensional (3D) datasets of the ultrasound data, where such datasets are accessed to present 2D and/or 3D images. Multiple consecutive 3D datasets may also be acquired and stored over time, such as to provide real-time 3D or four-dimensional (4D) display. The images may be modified and the display settings of the display 118 also manually adjusted using the user interface 124.

Figure 2:
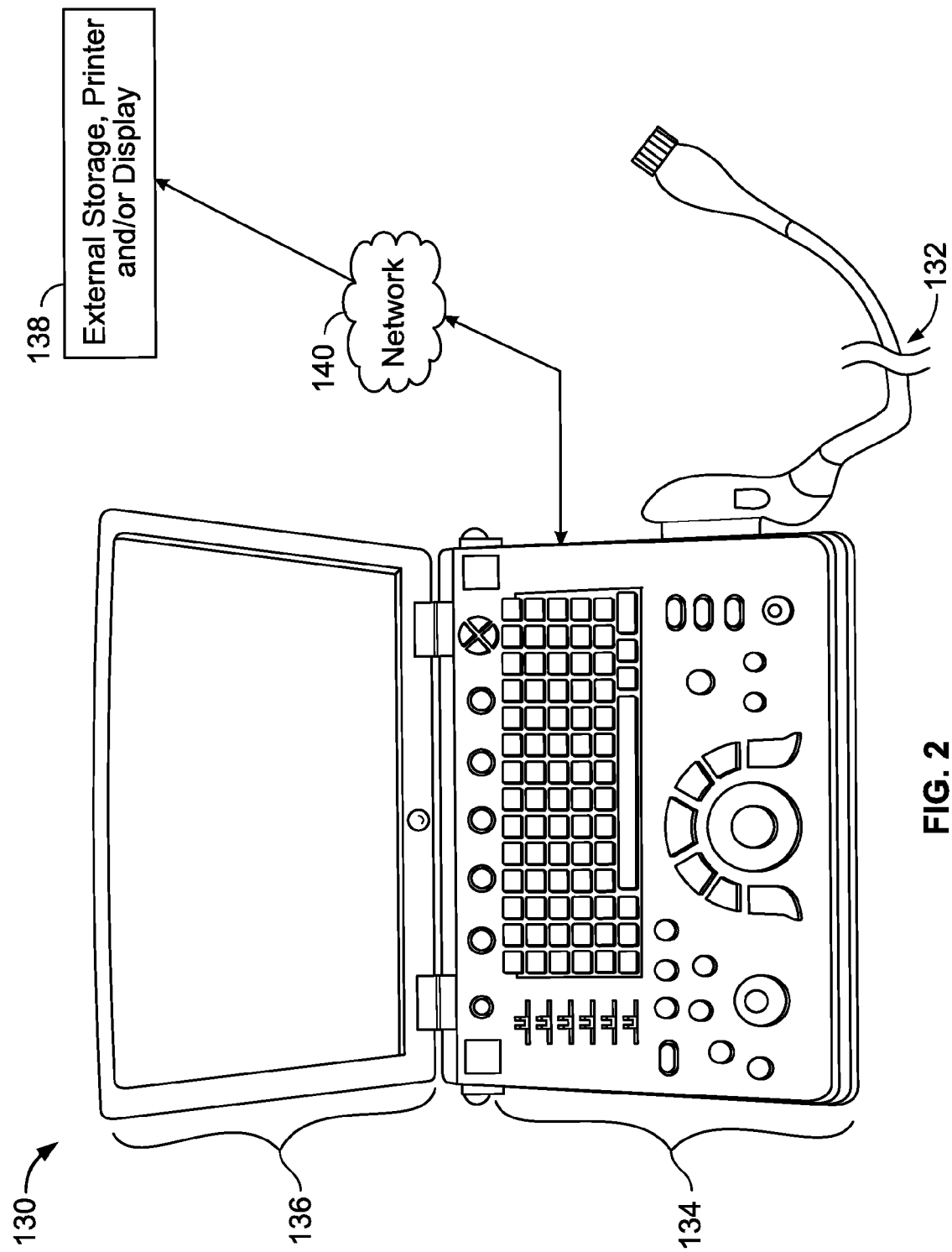
FIG. 2 illustrates a three-dimensional (3D) capable miniaturized ultrasound system formed in accordance with an embodiment of the present invention.

FIG. 2 illustrates a 3D-capable miniaturized ultrasound system 130 having a probe 132 that may include the matching layer structure. The probe 132 may be configured to acquire 3D ultrasonic data. For example, the probe 132 may have a 2D array of transducer elements 104 as discussed previously with respect to the probe 106 of FIG. 1. A user interface 134 (that may also include an integrated display 136) is provided to receive commands from an operator.

As used herein, "miniaturized" means that the ultrasound system 130 is a handheld or hand-carried device or is configured to be carried in a person's hand, pocket, briefcase-sized case, or backpack. For example, the ultrasound system 130 may be a hand-carried device having a size of a typical laptop computer, for instance, having dimensions of approximately 2.5 inches in depth, approximately 14 inches in width, and approximately 12 inches in height. The ultrasound system 130 may weigh about ten pounds, and thus is easily portable by the operator. The integrated display 136 (e.g., an internal display) is also provided and is configured to display a medical image.

The ultrasonic data may be sent to an external device 138 via a wired or wireless network 140 (or direct connection, for example, via a serial or parallel cable or USB port). In some embodiments, external device 138 may be a computer or a workstation having a display. Alternatively, external device 138 may be a separate external display or a printer capable of receiving image data from the hand carried ultrasound system 130 and of displaying or printing images that may have greater resolution than the integrated display 136. It should be noted that the various embodiments may be implemented in connection with a miniaturized ultrasound system having different dimensions, weights, and power consumption.

Figure 3:
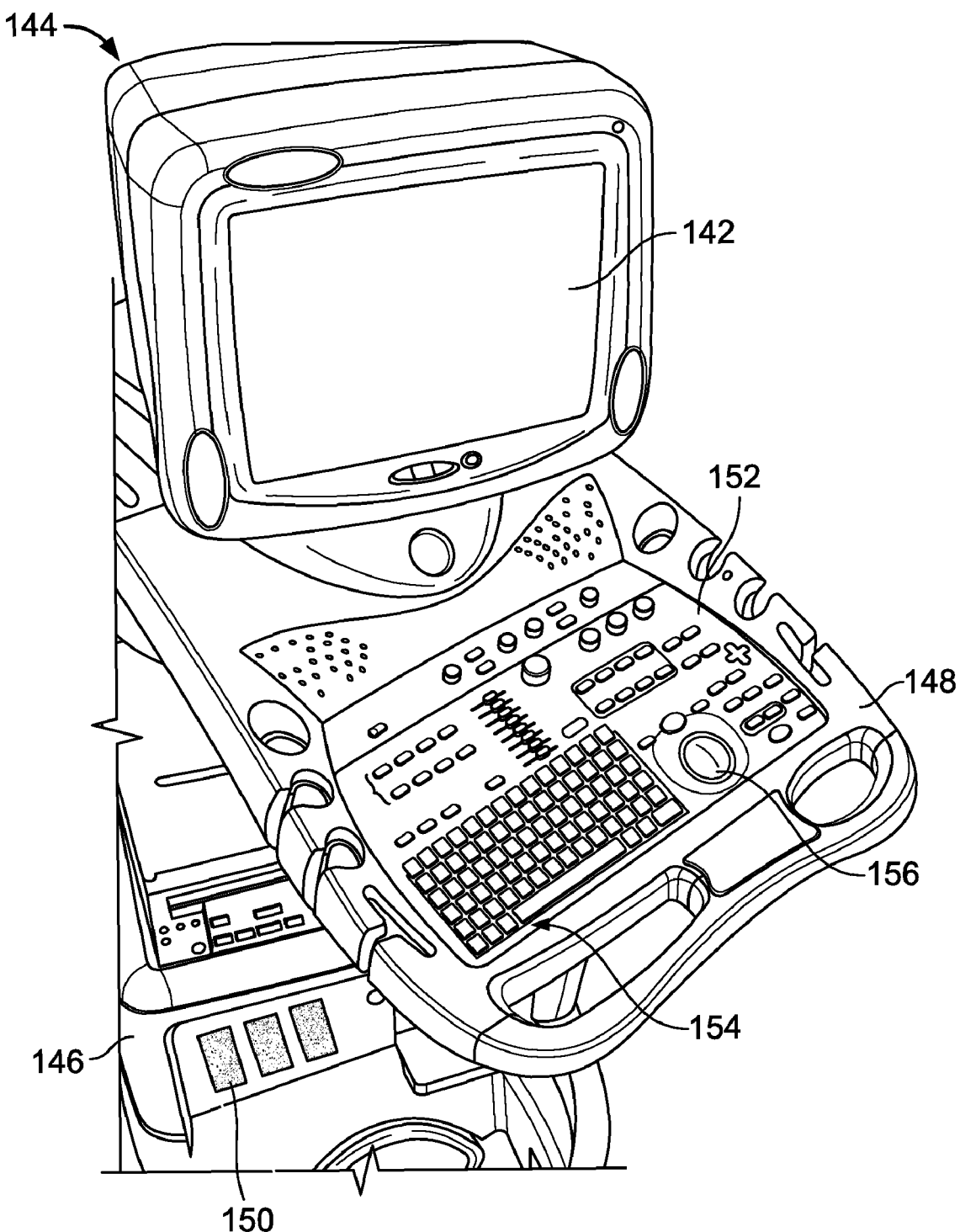
FIG. 3 illustrates a mobile ultrasound imaging system formed in accordance with an embodiment of the present invention.

FIG. 3 illustrates a mobile ultrasound imaging system 144 provided on a movable base 146. The ultrasound imaging system 144 may also be referred to as a cart-based system. A display 142 and user interface 148 are provided and it should be understood that the display 142 may be separate or separable from the user interface 148. The system 144 has at least one probe port 150 for accepting probes (not shown) that may include the matching layer structure.

The user interface 148 may optionally be a touchscreen, allowing the operator to select options by touching displayed graphics, icons, and the like. The user interface 148 also includes control buttons 152 that may be used to control the ultrasound imaging system 144 as desired or needed, and/or as typically provided. The user interface 148 provides multiple interface options that the user may physically manipulate to interact with ultrasound data and other data that may be displayed, as well as to input information and set and change scanning parameters. The interface options may be used for specific inputs, programmable inputs, contextual inputs, and the like. For example, a keyboard 154 and track ball 156 may be provided.

Figure 4:
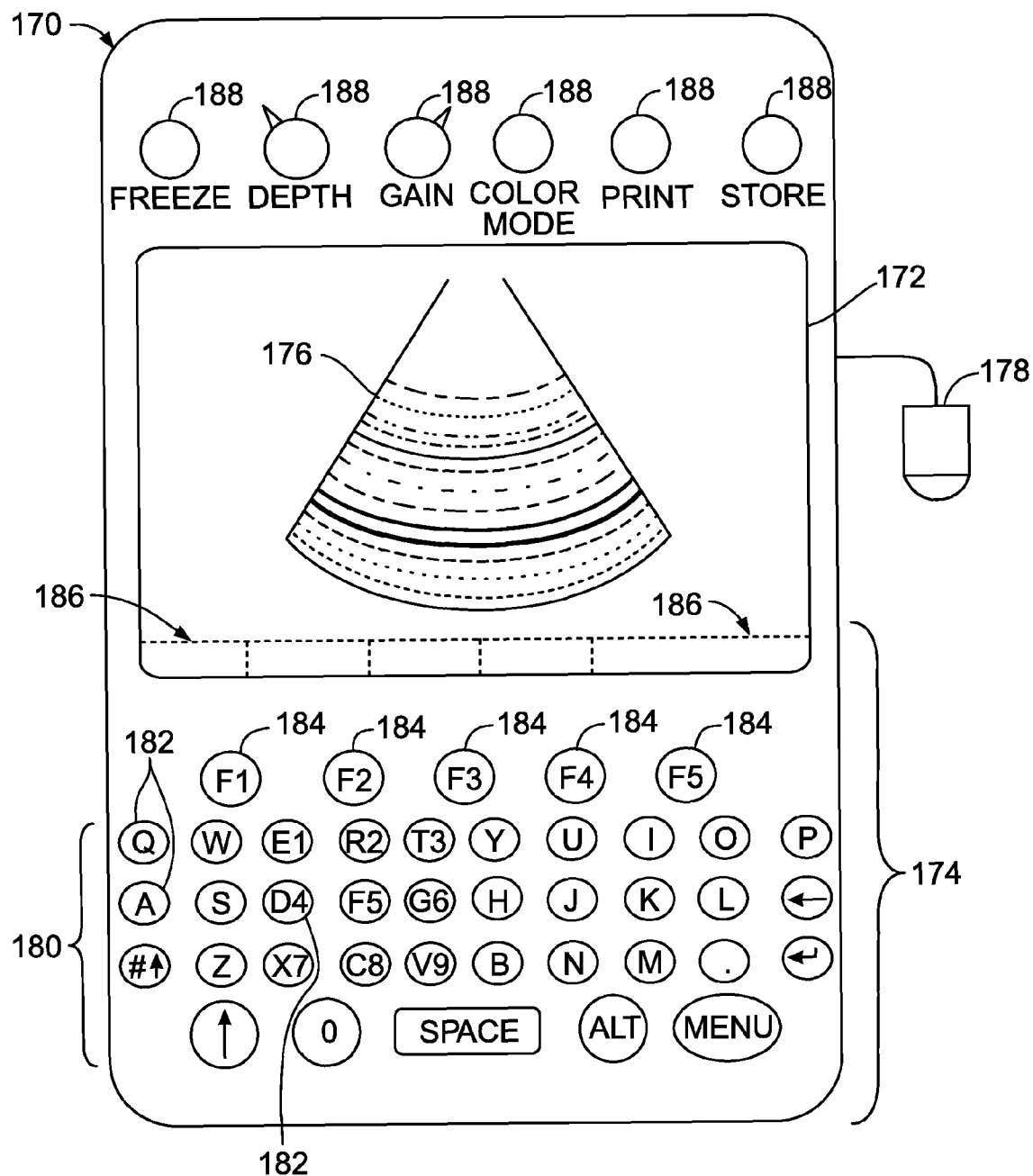
FIG. 4 illustrates a hand carried or pocket-sized ultrasound imaging system formed in accordance with an embodiment of the present invention.

FIG. 4 illustrates a hand carried or pocket-sized ultrasound imaging system 170 wherein display 172 and user interface 174 form a single unit. By way of example, the pocket-sized ultrasound imaging system 170 may be approximately 2 inches wide, approximately 4 inches in length, and approximately 0.5 inches in depth and weighs less than 3 ounces. The display 172 may be, for example, a 320×320 pixel color LCD display (on which a medical image 176 may be displayed). A typewriter-like keyboard 180 of buttons 182 may optionally be included in the user interface 174. A probe 178 that may include the matching layer structure is interconnected with the system 170.

Multi-function controls 184 may each be assigned functions in accordance with the mode of system operation. Therefore, each of the multi-function controls 184 may be configured to provide a plurality of different actions. Label display areas 186 associated with the multi-function controls 184 may be included as necessary on the display 172. The system 170 may also have additional keys and/or controls 188 for special purpose functions, which may include, but are not limited to "freeze," "depth control," "gain control," "color-mode," "print," and "store."

A matching layer structure as described herein may be used in an acoustical stack of the ultrasound probe 106 instead of at least one of the quarter-wavelength matching layers or a graded matching layer. A technical effect of at least one embodiment is that a mechanical equivalent based on lumped mechanical matching circuits (herein also referred to as lumped circuits) may be used to approximate the graded impedance taper that is realized by the matching layer structure. Practical realization of the lumped mechanical matching circuits is formed using a combination of thin material layers with selected mechanical properties. The assembly of the layers with different mechanical properties will mimic an equivalent mass and spring oscillator.

The matching layer structure comprises at least two sections of matching layer equivalents, herein referred to as matching layer sections. Each of the matching layer sections comprises at least two materials that may be formed in layers. The two materials are selected based on the mechanical properties of the materials. For example, one of the materials, herein referred to as a spring material, is a relatively low loss and low density material, such as a polymer or film, such as SU8™, an epoxy-based negative photoresist, or Kapton™, a polyimide material, and may have an acoustic impedance lower than 1.5 MegaRayls (MR). The other material, herein referred to as a mass material, is a relatively high density material such as tungsten, copper or other metal, and may have an acoustic impedance closer to 30 MR. It should be understood that other materials may be used. Each of the matching layer sections has a thickness that is much less than quarter-wavelength, e.g. approximately 50 micrometers (μm), although other thicknesses are contemplated.

The matching layer sections are formed by adjusting the amount or percentage of each of the materials in each of the matching layer sections. For example, the matching layer section with the highest impedance has the highest percentage of mass material and the lowest percentage of spring material, and the layer with the lowest impedance has the lowest percentage of mass material and the highest percentage of spring material. The matching layer section with the highest impedance is positioned closest to the piezoelectric layer within the stack and the matching layer section with the lowest impedance is positioned closest to the lens when matching to lower impedance medium.

FIG. 5 illustrates a matching layer structure 220 that has five equivalent matching layer sections. It should be understood that other numbers of matching layer sections may be used. The matching layer sections may be referred to as first matching layer section (ML1) 222, second matching layer section (ML2) 224, third matching layer section (ML3) 226, fourth matching layer section (ML4) 228 and fifth matching layer section (ML5) 230. The matching layer structure 220 has a thickness 276 and is included within an acoustical stack 270 that has at least a piezoelectric layer 272. A lens 274 may be formed on the stack 270. Although not shown, additional layers may be included within the stack 270, such as a dematching layer section, backing block, additional matching layers, such as a quarter-wavelength layer, and the like.

Each of the matching layer sections 222-230 has a thickness 232 that includes both mass and spring material. In one embodiment, each of matching layer sections 222-230 may have the same thickness 232. In another embodiment, the thicknesses 232 of the matching layer sections 222-230 may vary. It should be noted that the thicknesses of the matching layer sections 222-230 are shown for illustration purposes only and are not to scale with respect to the thicknesses of the piezoelectric layer 272 and the lens 274.

Each of the matching layer sections 222-230 comprises a mass layer and a spring layer. In some embodiments, one or more of the matching layer sections 222-230 may include only a mass layer or only a spring layer. The term "spring layer" refers to a material layer with a thickness and specific impedance that, when attached to the mass layer, results in a layer mechanical impedance acting mainly like a spring. The term "mass layer" refers a material layer with a thickness and specific impedance that, when attached to the spring layer, results in a layer mechanical impedance acting like a mass. The first matching layer section 222 includes spring layer 234 and mass layer 244. The second matching layer section 224 includes spring layer 236 and mass layer 246. The third matching layer section 226 includes spring layer 238 and mass layer 248. The fourth matching layer section 228 includes spring layer 240 and mass layer 250. The fifth matching layer section 230 includes spring layer 242 and mass layer 252. Each of the spring layers 234-242 and mass layers 244-252 has a thickness (discussed further below), although in some embodiments the thicknesses of each of the spring and mass layers may vary slightly across the matching layer section 222-230 based on manufacturing processes.

The ratio or percentage of mass material to spring material for each of the matching layer sections 222-230 may be changed to achieve a desired change in acoustic impedance along the transmission line. A bottom side 278 of the first matching layer section 222 is attached to the piezoelectric layer 272, such as with conductive glue, adhesive or other material. To match the acoustic impedance of the piezoelectric layer 272, the first matching layer section 222 has the highest impedance of any of the matching layer sections 222-230. To achieve the highest impedance, the first matching layer section 222 has the greatest percentage or proportion of the mass material compared to the other matching layer sections 222-230. Therefore, in general, for practical materials, a thickness 254 of the mass layer 244 is greater than the thickness of the mass layers 246-252 in any of the other matching layer sections 224-230 and, in general, for practical materials, the thickness 256 of the spring layer 234 is thinner than the thickness of the spring layers 236-242 in any of the other matching layer sections 224-230 when matching to a medium, such as water or the lens 274, that has lower impedance than the piezoelectric layer 272.

A bottom side 280 of the second matching layer section 224 is attached to a top side 282 of the first matching layer section 222. The acoustic impedance of the second matching layer section 224 is less than the impedance of the first matching layer section 222. To achieve the lower acoustic impedance, relatively less of the mass material is incorporated within the second matching layer section 224 than in the first matching layer section 222. Therefore, a thickness 258 of the mass layer 246 is thinner than the thickness 254 of the mass layer 244. Also, a thickness 260 of the spring layer 236 is greater than the thickness 256 of the spring layer 234. This pattern repeats throughout the matching layer structure 220 so that the fifth matching layer section 230 has the lowest acoustic impedance of any of the matching layer sections 222-230. To achieve the lowest acoustic impedance, the least amount of mass material is incorporated within the fifth matching layer section 230 when compared to all of the other matching layer sections 222-230. Therefore, a thickness 262 of the mass layer 252 is thinner than any of the other mass layers 244-250, and a thickness 264 of the spring layer 242 is thicker than any of the other spring layers 234-240. In other words, the spring layers 234-242 may have successively increasing thicknesses as the distance from the piezoelectric layer 272 increases, while the mass layers 244-252 may have successively decreasing thicknesses as the distance from the piezoelectric layer 272 increases. In another embodiment, the change in thicknesses may not be successive, that is, one or more spring layers 234-242 may have the same thickness as another spring layer 234-242 and one or more mass layers 244-252 may have the same thickness as another mass layer 244-252. In yet another embodiment, the thickness of one of the mass or spring layers may be held constant while the thickness of the other layer is decreased or increased.

Figure 6:
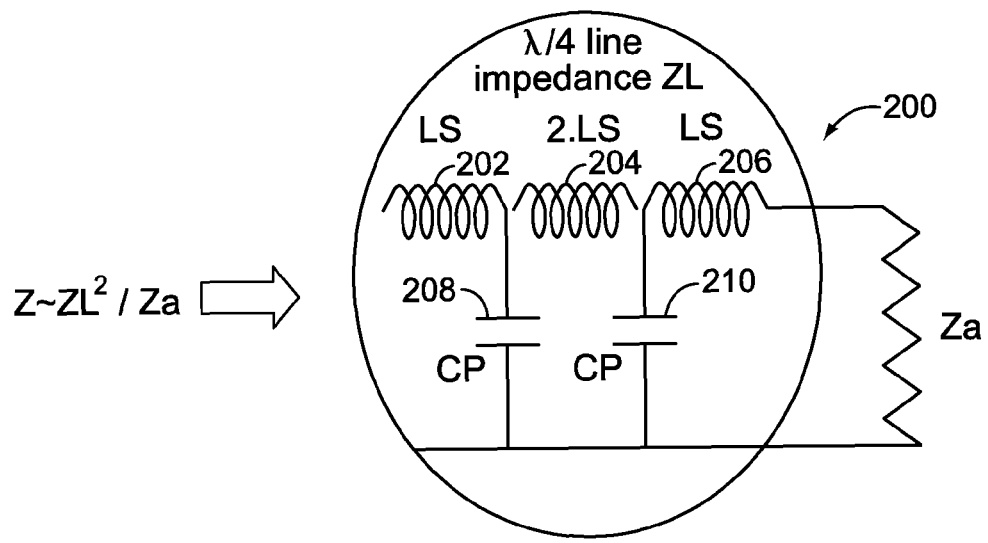
FIG. 6 illustrates a lumped circuit formed in accordance with an embodiment of the present invention for a quarter-wavelength transmission line that provides an electrical equivalent of the mechanical properties of matching layer sections that are used to build the matching layer structure of FIG. 5.

FIG. 6 illustrates a lumped circuit 200 for a quarter-wavelength transmission line that provides an electrical equivalent of the mechanical properties of the matching layer sections 222-230 used to build the matching layer structure 220 of FIG. 5. In other words, electronic components (e.g. inductor(s), capacitor(s), and the like) within the lumped circuit 200 may be used to estimate acoustical properties of the spring and mass layer materials. Therefore, the lumped circuit 200 shows the association of the spring layers 234-242 and mass layers 244-252. In this example, the lumped circuit 200 corresponds to one matching layer section 222-230 within the matching layer structure 220. Each of the matching layer sections 222-230 would be represented by a separate lumped circuit 200. The lumped circuit 200 has three inductors 202, 204 and 206 and two capacitors 208 and 210. In another embodiment, in the simplest form of the circuit 200, a single inductor and a single capacitor may be used, and in other embodiments, different numbers of inductors and capacitors may be used. The spring layer 234-242 may be characterized by the capacitance of the capacitors 208 and 210 and the mass layer 244-252 may be characterized by the inductance of the inductors 202-206.

The example shown in FIG. 6 simulates three mass layers (inductors) and two spring layers (capacitors) to mimic a quarter-wavelength layer function, but it should be understood that this function may be achieved with other configurations depending upon at least the desired relative bandwidth. In the simplest configuration as discussed above, a single inductor and a single capacitor may be used. FIG. 6 may be used to illustrate physical understanding of the structure of the matching layer section. The general solution may also be analyzed through the classical LC ladder filters theory.

An electrical equivalent of the mechanical properties of a mass layer and a spring layer used to build a matching layer section 222-230 is provided in Equations (Eq.) 1 and Eq. 2.

$$LS := \frac{ZL \cdot 4}{\omega r \cdot \pi^2} \quad (1)$$

$$CP := \frac{1}{ZL \cdot \omega r \cdot \sqrt{2}} \quad (2)$$

Therefore, the value of the inductance (LS) and capacitance (CP) of the lumped circuit 200 example is based upon a line impedance (ZL) (e.g. acoustic impedance) of the matching layer section 222-230 and the resonant frequency ωr of the center frequency of the probe 106. The quarter wavelength effect is achieved by the serial association of (LS+CP) and (2*LS+CP) cells. The ZL may be a selected or predetermined impedance value or calculated as discussed further below.

The combination of the electrical equivalents of a mass layer and a spring layer provides the characteristics to model one of the matching layer sections 222-230. Eq. 1 and Eq. 2 are repeated to calculate LS and CP for each of the matching layer sections 222-230, wherein each of the matching layer sections 222-230 has a different ZL. As discussed previously, ZL decreases with each matching layer section 222-230 in the direction away from the piezoelectric layer 272. Therefore, at least two circuits 200 with appropriate components may be cascaded with respect to each other to achieve large bandwidth matching around the resonant frequency ωr. The LS and CP values for each matching layer section 222-230 may be used in an electrical simulation of a proposed acoustical stack 270, also referred to as Mason model, allowing electrical elements to be matched to acoustical structures.

FIGS. 7-10 illustrate acoustical simulations of the bandwidth performance based on the matching layer structure 220 within the stack 270. When calculating the simulation, the thickness 276 of the matching layer sections 222-230 may be based on a classical Mason model without optimization of material properties, that is, without taking into account diffraction laws and lens attenuation in the matching layer sections 222-230. The acoustical simulations 300, 302, 330 and 332 may be calculated using the inductance and capacitance values calculated in Eq. 1 and Eq. 2, respectively.

When designing the probe 106, the stack structure may be simulated so that the least number of matching layer sections 222-230 may be identified that are needed to satisfy the probe specification. Fewer matching layer sections result in less thickness 276, which improves attenuation. One parameter that may be specified is the desired bandwidth at −6 decibels (dB) and at −20 dB. Other parameters may also be considered.

Figure 7:
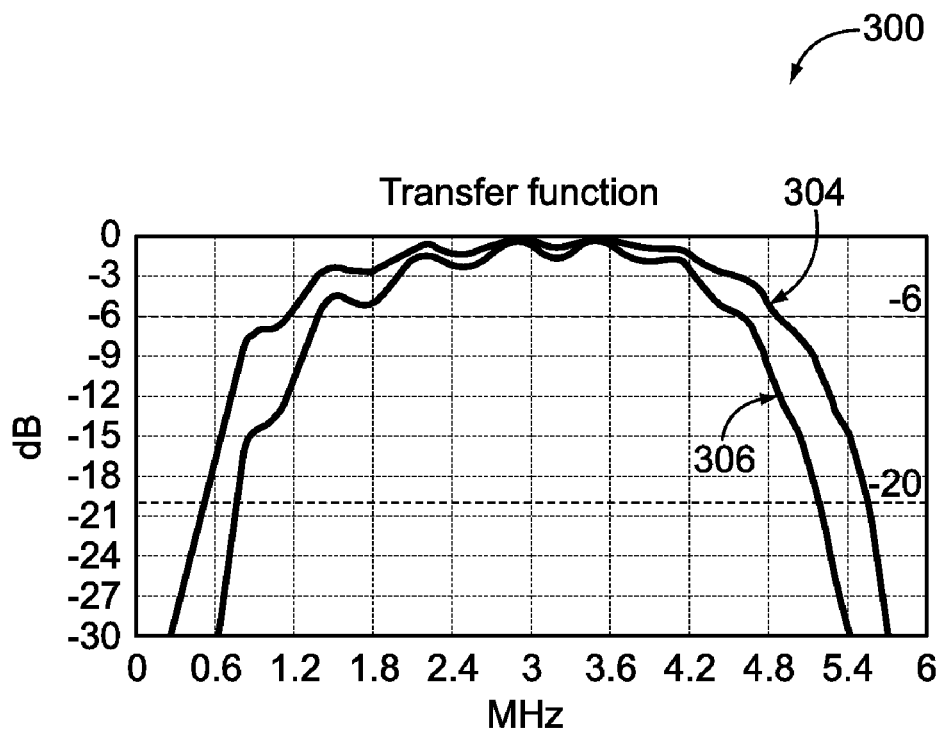
FIGS. 7-10 illustrate acoustical simulations of the bandwidth performance based on the matching layer structure of FIG. 5 in accordance with an embodiment of the present invention.
Figure 8:
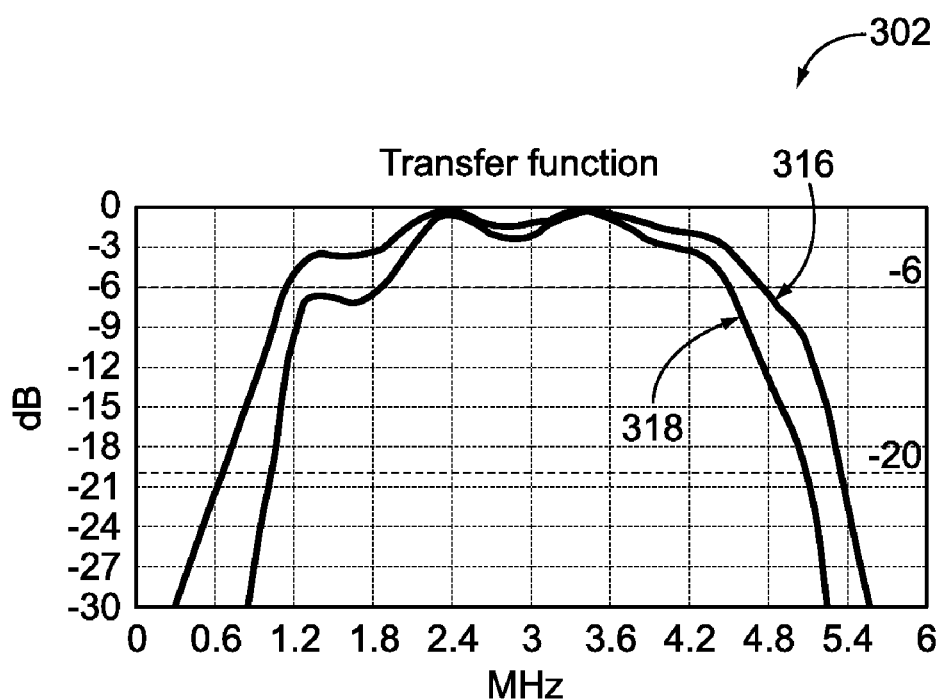

FIGS. 7 and 8 illustrate acoustical simulations 300 and 302, respectively, of a probe transfer function calculated based on a probe 106 that incorporates the matching layer structure 220 within the stack 270. In FIG. 7, ten matching layer sections 222-230 are used, having a total thickness 276 of 500 μm. In FIG. 8, five matching layer sections 222-230 are used, having a total thickness 276 of 250 μm. The simulations are based on a 3 megahertz (MHz) center frequency array.

FIG. 7 shows a simple or one-way transmission line 304 and a two-way transmission line 306. FIG. 8 shows a one-way transmission line 316 and a two-way transmission line 318. The two-way transmission lines 306 and 318 show a decrease in bandwidth due to the ultrasound signal traveling through the stack 270 two times (e.g. transmit and receive signals). In other words, the overall attenuation is greater when the transmit and receive signals are considered. Because there are more matching layer sections in FIG. 7, the lines 304 and 306 have more ripple across the bandwidth compared to the lines 316 and 318. In one embodiment, ripple amplitude may be reduced by fine adjustment of layer properties using, for example, ladder filters synthesis algorithms. The bandwidths may be compared, such as between the two-way transmission lines 306 and 318, to determine whether the matching layer structure that has five matching layer sections provides the desired performance. Additional simulations may be conducted using less than five matching layer sections or any number of matching layer sections between five and ten matching layer sections. Also, matching layer structures 220 having greater than ten matching layer sections are contemplated. In some embodiments, simulations may be conducted to identify the least number of matching layer sections 222-230 that will satisfy the probe specification.

Figure 9:
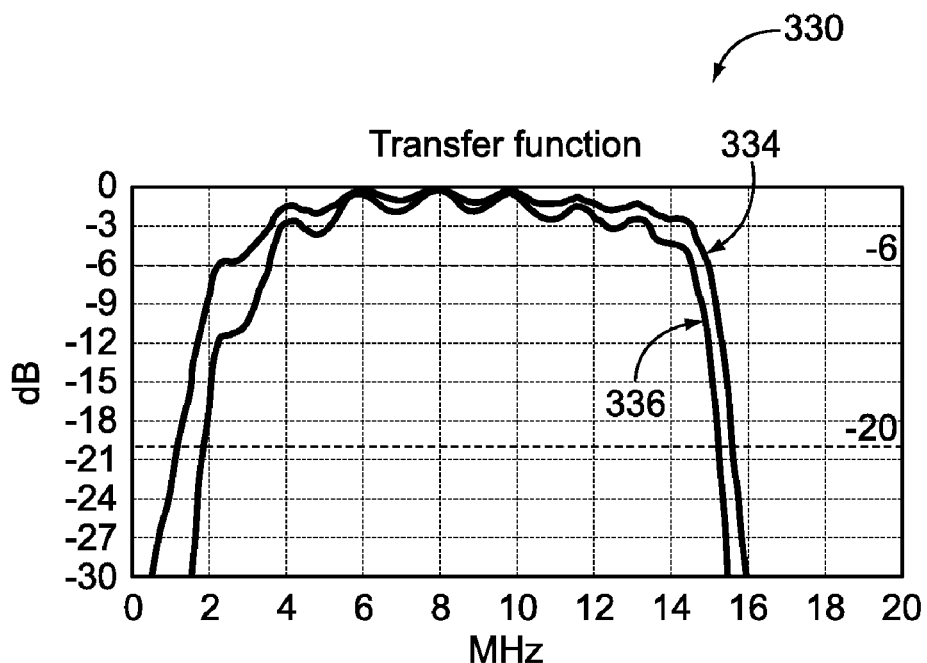
Figure 10:
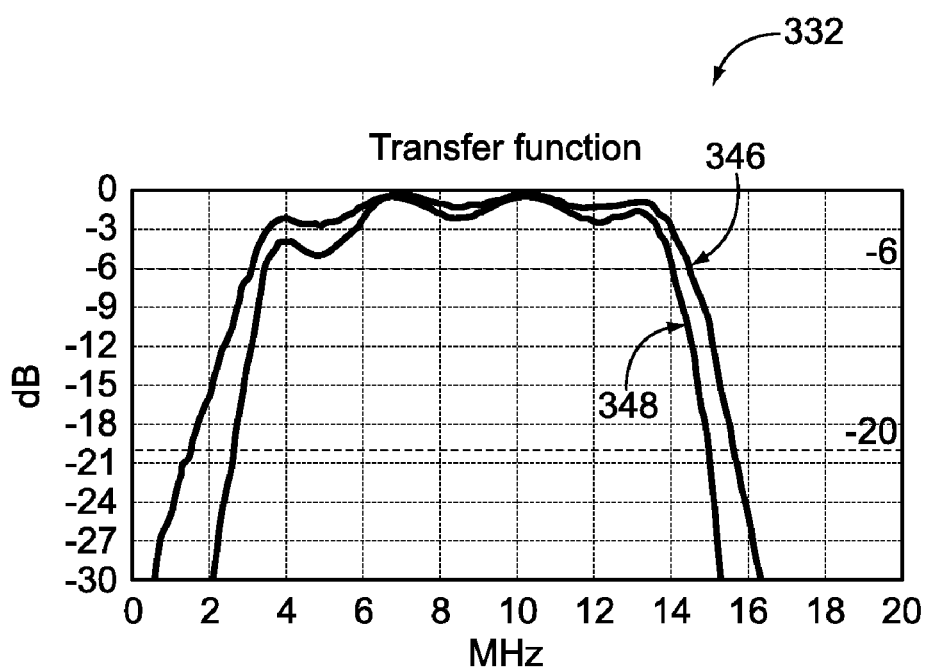

Similarly, FIGS. 9 and 10 illustrate acoustical simulations 330 and 332, respectively, of a probe transfer function calculated based on a probe 106 that incorporates the matching layer structure 220 within the stack 270. The simulations 330 and 332 are based on an eight MHz center frequency array. In FIG. 9, ten matching layer sections 222-230 are used, having a total thickness 276 of 500 µm. In FIG. 10, five matching layer sections 222-230 are used, having a total thickness 276 of 250 µm.

FIG. 9 shows a one-way transmission line 334 and a two-way transmission line 336. FIG. 10 shows a one-way transmission line 346 and a two-way transmission line 348. Again, the bandwidth performance between the two simulations 330 and 332 may be compared to identify the least number of matching layer sections 222-230 that satisfy the probe specification.

The conversion of the transmission line parameters into mechanical properties, that is, mass-spring oscillation modes rather than purely electric transmission line parameters as in Eq. 1 and Eq. 2, such as inductance and capacitance, is achieved by the association of the heavy material (mass) with the elastic material (spring) in a bi-layer structure (e.g. one of the matching layer sections 222-230) that will be the equivalent of a single quarter-wavelength matching layer. The relation between the targeted acoustic impedance ZL of the bi-layer structure and the effective mechanical thickness of each of the two layers may be determined using Eq. 3 and Eq. 4.

$$Tmass(n) := \frac{\lambda m}{2 \cdot \pi} \cdot \frac{ZL \cdot \left(1 - \frac{zs^2}{ZL^2}\right)}{zm} \quad (3)$$

$$Tspring(n) := \frac{\lambda s}{2 \cdot \pi} \cdot \frac{zs}{ZL} \quad (4)$$

Eq. 3 gives the thickness of the mass layer (Tmass) as a function of matching layer impedance (ZL), the heavy or mass (m) material properties and the spring (s) material properties, namely, wavelength of the mass material ($\lambda m$), acoustic impedance of the mass material (zm), and acoustic impedance of the spring material (zs). Eq. 4 gives the thickness of the spring layer (Tspring) as a function of the matching layer impedance (ZL) and the spring (s) material properties, namely, wavelength of the spring material ($\lambda s$) and acoustic impedance of the spring material (zs). Eq. 3 and Eq. 4 may be used to describe each of the matching layer sections 222-230 by changing the matching layer impedance.

Figure 11:
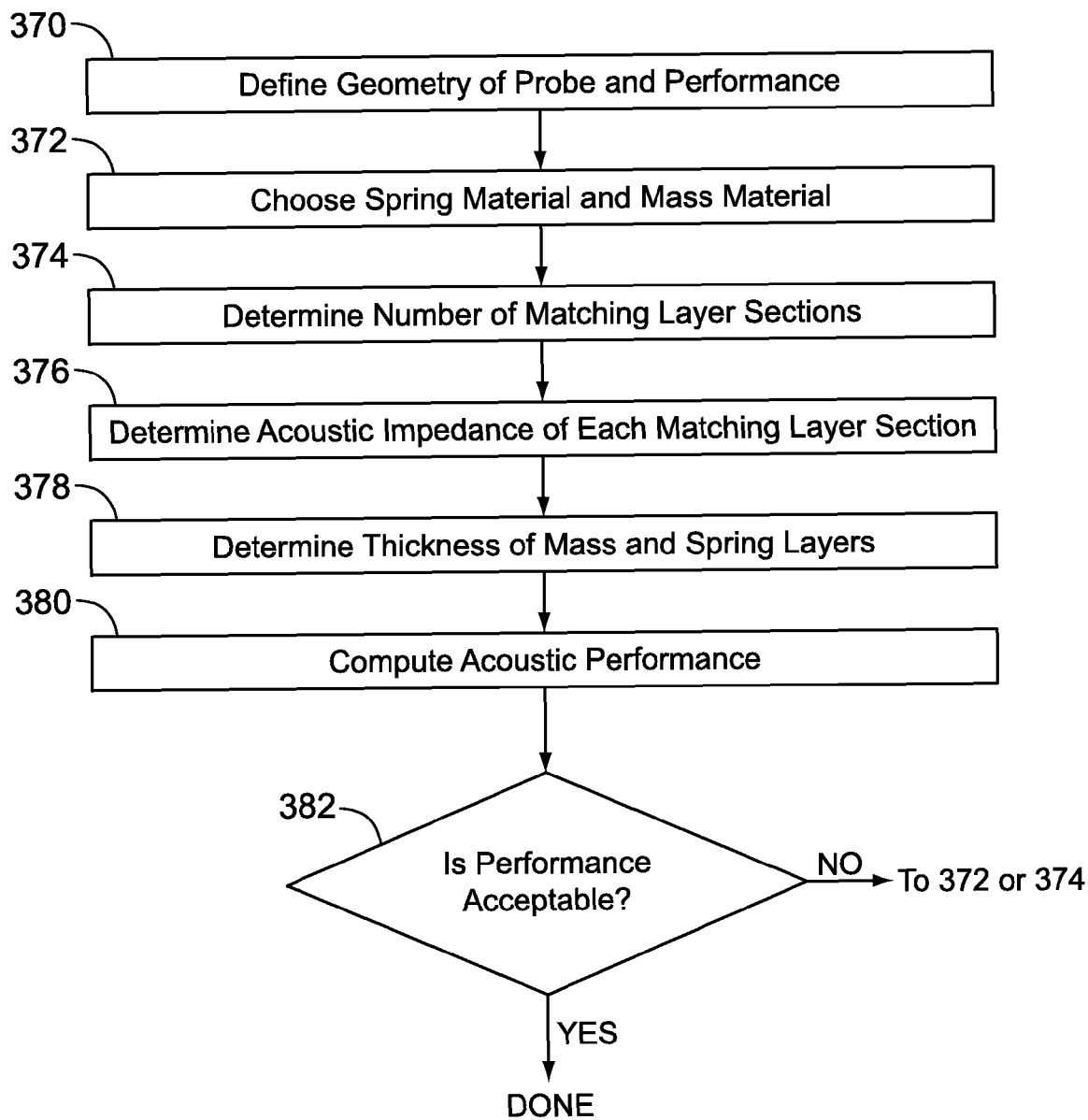
FIG. 11 illustrates a method for determining the number of matching layer sections to include within the matching layer structure of a probe in accordance with an embodiment of the present invention.

FIG. 11 illustrates a method for determining the number of matching layer sections 222-230 to include within the matching layer structure 220 of a probe 106. At 370 the geometry of the probe 106 is determined as well as the target or desired performance. For example, the center frequency is selected. Also, the percentage of bandwidth may be specified, such as the percentage of bandwidth at each of −6 db and −20 db.

At 372, materials are chosen for the spring layer 234-242 and the mass layer 244-252. For example, SU8™ may be selected for the spring material and tungsten may be selected for the mass material. Other materials may be used. In one embodiment, the same spring material may be used in all of the spring layers 234-242 and the same mass material may be used in all of the mass layers 244-252. In another embodiment, a different spring and/or mass material may be used in one or more of the layers 234-252.

At 374 the number of matching layer sections 222-230 to be simulated is determined. As discussed previously, the probe performance may be simulated using different numbers of matching layer sections 222-230 in order to determine the minimum number of matching layer sections 222-230 that will provide the desired performance. Alternatively, a predetermined number of matching layer sections 222-230 may be selected, such as three, five or ten matching layer sections 222-230. In another embodiment, two or three matching layer sections 222-230 may be selected as the minimum number of matching layer sections 222-230 to be considered.

At 376, acoustic impedances for each of the matching layer sections 222-230 may be determined. In one embodiment, the acoustic impedances for each of the matching layer sections 222-230 may be based upon an exponentially decreasing acoustic impedance, a regularly decreasing acoustic impedance, or any other curve that decreases the acoustic impedance from the high acoustic impedance of the piezoelectric layer (which in one embodiment may be 30 MRay) to the low acoustic impedance of the lens (which in one embodiment may be 1.5 MRay). In another embodiment, for dematching technology, the target acoustic impedances for the matching layer sections 222-230 may be determined using the following Eq. 5 and Eq. 6:

$$ZRCKSym(N, k) := \left[\left[ZC \cdot \left(1 - k^2 + \frac{8}{\pi^2} \cdot k^2\right)^2 \cdot \omega r(k)\right]^{2 \cdot N} \cdot ZR\right]^{\frac{1}{2 \cdot N + 1}} \quad (5)$$

$$ZmL\_(N, n, k) := \left(\frac{ZRCKSym(N, k)}{ZR}\right)^{\frac{2 \cdot (N-n)+1}{2 \cdot N}} \cdot ZR \quad (6)$$

wherein ZC is the acoustic impedance of the piezoelectric layer 272, ZR is the acoustic impedance of radiation medium, $\omega r(k)$ is the resonance frequency (pulsation) that is piezoelectric coupling coefficient dependent, k is a coupling coefficient, N is the number of matching layer sections, n is a counter for nth matching layer section, counting from the piezoelectric layer 272 towards the lens 274, and ZmL_(N,n,k) is the acoustic impedance of the nth matching layer section. Therefore, the acoustic impedances of the matching layer sections 222-230 may be based on at least one of resonant frequency ($\omega r$) of the probe 106, acoustic impedance of the piezoelectric layer 272 (or the acoustic impedance of a quarter-wavelength matching layer, if used) and acoustic impedance of the lens 274. It should be understood that the acoustic impedances of the matching layer sections 222-230 may be determined using different equations for other technologies. In another embodiment, different materials may be selected for one or more of the matching layer sections 222-230. For example, a spring material having a relatively lower impedance may be selected for the layer closest to the lens 274 while a different spring material having a relatively higher impedance may be selected for the matching layer section(s) nearest the piezoelectric layer 272.

In one embodiment, at 378 the thicknesses of each of the mass layers 244-252 and spring layers 234-242 within each of the matching layer sections 222-230 may be determined based on the acoustic impedances, such as with Eq. 3 and Eq. 4. Therefore, it can be determined whether the overall thickness 276 of the matching layer structure 220 is acceptable, resulting in an allowable amount of signal attenuation. Also, the mass layers 244-252 and spring layers 234-242 are formed during manufacturing processes as discussed further below and in some embodiments there may be limitations based on the material properties and the manufacturing capabilities for forming certain layers of materials within certain tolerances.

At 380 the acoustic performance is computed, such as by using the capacitance and inductance calculated in Eq. 1 and Eq. 2 to generate the graphs of FIGS. 7-10. At 382 it is determined whether the acoustic performance is acceptable. In addition, it may be determined whether the thicknesses of the mass layers 244-252 and spring layers 234-242 are acceptable, as well as the overall thickness 276 of the matching layer structure 220. In one embodiment, if the bandwidth performance is not acceptable, the method may return to 374 to specify a greater number of matching layer sections 222-230. In another embodiment, if the bandwidth performance is acceptable, the method may return to 374 to specify a lesser number of matching layer sections 222-230 in order to determine if the thinnest matching layer structure 220 has been identified. For example, it is desirable to have the lowest number of matching layer structures, and thus the least amount of signal attenuation (e.g. propagation losses), while still meeting the performance of the probe 106. Also, less matching layer sections 222-230 may be easier to manufacture and result in lower cost. In some embodiments, the method of FIG. 11 may be accomplished multiple times, selecting different numbers of matching layer sections 222-230, to determine the lowest number of matching layer sections 222-230 that will achieve the target performance. In yet another embodiment, the method may return to 372 to choose different materials for one or more of the mass layers 244-252 and spring layers 234-242 if, for example, the performance is not acceptable or the matching layer structure 220 may be difficult to achieve based on available manufacturing technologies.

In another embodiment, a stack may be formed that includes a quarter-wavelength matching layer. FIG. 12 illustrates an acoustical stack 400 including both a matching layer structure 402 and a quarter-wavelength matching layer 404. A bottom side 406 of the quarter-wavelength matching layer 404 is attached to a top side 408 a piezoelectric layer 410 and the matching layer structure 402 is attached to a top side 412 of the quarter-wavelength matching layer 404.

In one embodiment, the quarter-wavelength matching layer 404 may be included within the stack 400 to provide additional flexibility when choosing the spring material. For example, a spring material may be selected that has a relatively lower impedance allowing a better impedance match for the matching layer section within the matching layer structure 402 nearest lens 414.

In another embodiment, the quarter-wavelength matching layer 404 may be positioned between the matching layer structure 402 and the lens 414.

There are several methods that may be used to form the mass layers 244-252 and spring layers 234-242 within the matching layer structure 220 and 402. One method used is based on micro-electronic technologies and wafer processing. Spring material may be a photoresist that has been specially treated, for example, loading added, to have the density/speed properties that fit the acoustic impedance requirement of the spring material. Mass material may be a metal with density/speed properties that fit the acoustic impedance requirement of the mass material. The mass material may be any relatively dense and stiff material such as, but not limited to, tungsten. Both the mass and spring materials need to be compatible with variable thickness sandwich manufacturing.

In one embodiment, a photoresist or polymer, such as SU8™, may be used as the spring material and can be patterned using micro electronic photolithography. For example, a layer of SU8™ may be spin coated to form the desired thickness. In another embodiment, to lower the material density a dot pattern may be accomplished on one or more of the matching layer sections 222-230 that are closer to the lens 274, in order to reach the desired density. In yet another embodiment, the metal forming the mass layer may be vacuum deposited.

The matching layer structure 220 may be formed separate from the other layers of the stack 270. In one embodiment, a layer of silicon dioxide (SiO2) may be deposited on a silicon wafer used for building the matching layer structure 220. During masking and etching operations conducted to build the matching layer structure 220, a hole may be formed that runs or extends through the entire matching layer structure 220. When all of the mass layers 244-252 and spring layers 234-242 have been formed, SiO2 etching solution may be fed through the hole to the SiO2 layer. Complete etching of the SiO2 layer will free the matching layer structure 220 from the silicon wafer.

In another embodiment, the matching layer structure 220 may be formed through lamination. Therefore, the spring layer 234-242 may be formed using a preformed layer of material, such as Kapton™, and the mass layer 244-252 may be formed using a preformed layer of a metal material such as copper. Different thicknesses of the spring layers 234-242 and mass layers 244-252 may be used to form the different matching layer sections 222-230 to achieve the desired acoustic impedance. A layer of metal material (e.g. mass layer 244) may be laminated over a layer of spring material (e.g. spring layer 234) to form the first matching layer section 222. A second layer of spring material (e.g. spring layer 236) may be laminated over the layer of metal material (e.g. mass layer 244), and a second layer of metal material (e.g. mass layer 246) may be laminated over the second layer of spring material (e.g. spring layer 236), and so on.

In yet another embodiment, the matching layer structure 220 may be formed using digital micro printing, which is a technology that allows the deposition of materials.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for forming a impedance matching layer structure of an acoustical stack for an ultrasound probe, the method comprising:
   forming a first impedance matching layer section, for an ultrasound probe, comprising a spring layer at a bottom side of the first matching layer section and a mass layer at a top side of the first matching layer section, the bottom side of the first matching layer section configured to be attached to one of a piezoelectric layer or a quarter-wavelength matching layer, the spring layer comprising a spring material and the mass layer comprising a mass material that has higher impedance than the spring material; and
   forming at least one additional impedance matching layer section, for an ultrasound probe, comprising a spring layer at a bottom side of the additional matching layer section and a mass layer at a top side of the additional matching layer section, the bottom side of the additional matching layer section configured to be attached to the top side of the first matching layer section, the spring layer comprising the spring material and the mass layer comprising the mass material.

2. The method of claim 1, wherein the first matching layer section comprises a greater percentage of the mass material and a lesser percentage of the spring material than the additional matching layer section.

3. The method of claim 1, wherein a number of the additional matching layer sections is based on a bandwidth of the probe.

4. The method of claim 1, further comprising:
   determining acoustic impedances of the first matching layer section and the additional matching layer section; and
   determining thicknesses of the mass layers based on the acoustic impedance of at least one of the first matching layer section or the additional matching layer section, and at least one material property of the mass material or a material property of the spring material of the first matching layer section or the additional matching layer section.

5. The method of claim 1, further comprising:
   determining acoustic impedances of the first matching layer section and the additional matching layer section; and
   determining thicknesses of the spring layers based on the acoustic impedances and at least one material property of the spring material of the first matching layer section or the additional matching layer section.

6. The method of claim 1, wherein the spring material has an associated acoustic impedance and wherein the mass material has an associated acoustic impedance and material wavelength, the method further comprising determining a thickness of the mass layer based on the material wavelength of the mass material of the first matching layer section or the additional matching layer section, the acoustic impedance of the mass material of the first matching layer section or the additional matching layer section and the acoustic impedance of the spring material of the first matching layer section or the additional matching layer section.

7. The method of claim 1, wherein the spring material, of the first matching layer section or the additional matching layer section, has an associated acoustic impedance and material wavelength, the method further comprising determining a thickness of the spring layer based on the material wavelength of the spring material and the acoustic impedance of the spring material.

8. The method of claim 1, further comprising determining the acoustic impedance of each of the matching layer sections based on one of an exponentially decreasing acoustic impedance and a linearly decreasing impedance.

9. The method of claim 1, further comprising determining the acoustic impedance of each of the matching layer sections based on an acoustic impedance of one of the piezoelectric layer and the quarter-wavelength matching layer and an acoustic impedance of water.

10. The method of claim 1, wherein an acoustic performance of the stack is based on modeling the matching layer structure using a lumped circuit for a quarter-wavelength transmission line, a total number of the matching layer sections being based on the acoustic performance of the stack.

11. The method of claim 1, further comprising:
   determining an inductance and a capacitance for each of the first matching layer section and the additional matching layer section based on an acoustic impedance of the first matching layer section and the additional matching layer section, respectively, and a resonant frequency of the probe; the inductance configured to characterize the spring layer of the first matching layer section or the additional matching layer section and the capacitance configured to characterize the mass layer of the first matching layer section or the additional matching layer section; and
   determining an acoustic performance of the stack based on the inductance and the capacitance.

* * * * *